United States Patent
Biffoni et al.

(10) Patent No.: US 6,500,422 B2
(45) Date of Patent: *Dec. 31, 2002

(54) METHODS FOR PREVENTING GRAFT REJECTION IN TRANSPLANTATION AND FOR PRODUCING A UNIVERSAL GENE THERAPY HOST CELL USING LYMPHOCYTE ACTIVATION (LAG-3)

(75) Inventors: Mauro Biffoni, Rome (IT); Ruben Papoian, Villars-sous-Yens (CH)

(73) Assignee: Applied Research Systems ARS Holding N.V., Curacao (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,147

(22) PCT Filed: Nov. 29, 1996

(86) PCT No.: PCT/EP96/05280

§ 371 (c)(1),
(2), (4) Date: Dec. 1, 1999

(87) PCT Pub. No.: WO98/23748

PCT Pub. Date: Jun. 4, 1998

(65) Prior Publication Data

US 2002/0081282 A1 Jun. 27, 2002

(51) Int. Cl.$^7$ .......................... A61K 48/00; C12N 5/00; C12N 5/08; C12N 15/63

(52) U.S. Cl. .................... 424/93.21; 435/328; 435/455; 435/325

(58) Field of Search .......................... 424/93.21; 514/44; 435/328, 69.1; 536/23.5; 800/4

(56) References Cited

U.S. PATENT DOCUMENTS 5,876,708 A * 3/1999 Sachs ........................ 424/93.1

FOREIGN PATENT DOCUMENTS

| EP | WO 98/23748 | * | 6/1998 |
| WO | 9110682 | | 7/1991 |
| WO | 9530750 | | 11/1995 |

OTHER PUBLICATIONS

TE Mollnes et al., Molecular Immunology, "Xenotransplantation: how to overcome the complement obstacle?" Mini Review, (1999) 36, pp. 269–276.*

K Prelle et al., Cells Tissues Organs, "Establishment of Pluripotenet Cell Lines from Vertebrate Species–Present Status and Future Prospects," 1999, 165:220–236.*

S Brouard et al., Review Article, "T Cell Response in Xenorecognition and Xenografts: A Review," Human Immunology, 1999, 60, pp. 455–468.*

MR Capecchi, Scientific American, "Targeted Gene Replacement," Mar. 1994, pp. 52–59.*

Eck et al., "Gene–based therapy." Goodman & Gilman's The Pharmacological Basis of Therapeutics– Ninth Edition, McGraw–Hill: 77–101, 1996.*

Mullins et al., "Perspectives Series: Molecular Medicine in Genetically Engineered Animals." J. of Clin. Investigation, vol. 98 (11): S37–S40, 1996.*

Wall R.J., "Transgenic Livestock: Progress and Prospects for the Future." Theriogenology, vol. 45:57–68, 1996.*

Platt JL., "Prospects for xenotransplantation". Pediatric Transplantation, vol. 3 (3): 193–200, Aug. 1999.*

Baixeras et al., "Characterization of the Lymphocyte Activation Gene 3–Encoded Protein. A new Ligand for Human Leukocyte Antigen Class II Antigens", *J. Exp. Med.*, vol. 176, pp.327–337, (1992).

Strehlau et al., "Expression of the Lymphocyte Activation Gene 3 (LAG3) and TH–1/TH–2 Type Cytokines in Clinical Renal Allograft Rejection.", *Journal of the American Society*, vol. 7, No. 9, pp.1046–6673, (1996).

Annunziato et al., "Expression and release of LAG–3–encoded protein by human CD4 T cells are associated with IFN–y production", *FASEB Journal*, vol. 10, No. 7, pp. 769–776, (1996).

Huard et al., Cellular expression and tissue distribution of the human LAG–3–encoded protein, an MHC class II Ligand, *Immunogenetics*, vol. 39, pp.213–217, (1994).

Mastrangeli et al., "Cloning of Murine LAG–3 by Magnetic Bead Bound Homologous Probes and PCR (Gene–Capture PCR)", *Analytical Biochemistry*, vol. 241, pp.93–102, (1996).

Miyazaki et al., "Independent Modes of Natural Killing Distinguished in Mice Lacking Lag3", *Science*, vol. 272 pp.405–408, (1996).

Huard et al., "T cell major histocompatibility complex class II molecules down–regulated CD4 T cell clone responses following LAG–3 binding", *Eur. J. Immunol*, vol. 26, pp. 1180–1186, (1996).

(List continued on next page.)

Primary Examiner—Ram R. Shukla
(74) Attorney, Agent, or Firm—Browdy and Neimark, PLLC

(57) ABSTRACT

A method to prevent graft rejection of transplanted cells, tissues or organs without general immunosuppression is described. The method employs a newly discovered protein, LAG-3. When allogeneic or xenogeneic cells are engineered to express LAG-3 on their surface and transplanted, immune destruction of the implanted cell, tissue or organ is prevented, while the host's immune system remains functional. A particular application of this method allows the preparation of a universal gene therapy host cell expressing LAG-3 on its surface for protection from graft rejection by a host's immune system.

5 Claims, 2 Drawing Sheets

OTHER PUBLICATIONS

Triebel et al., "LAG–3, A novel Lymphocyte Activation Gene Closely Related to CD4", *J. Exp. Med.*, vol. 171 pp.1393–1405, (1990).

Huard et al., "Lymphocyte–activation gene 3/major histocompatibility complex class II interaction modulates the antigenic response of CD4 T Lymphocytes", *Eur. J. Immunol.*, vol. 24, pp.3216–3221, (1994).

Miyazaki et al., "LAG–3 is not responsible for selecting T helper cells in CD4–deficient mice", International Immunology, vol. 8, pp.725–729, (1995).

Suzuki et al., "Viral Interleukin 10 (IL–10), the Human Herpes Virus 4 Cellular IL–10 Homologue, Induces Local Anergy to Allogeneic and Syngeneic Tumors", *J. Exp. Med.*, vol. 182, pp.477–486, (1995).

Bellgrau et al., "A role for CD95 ligand in preventing graft rejection", *Letters to Nature*, vol. 377, pp.630–632, (1995).

Lau et al., "Prevention of Islet Allograft Rejection with Engineered Myoblast Expressing FasL in Mice", *Science*, vol. 273, pp. 109–112, (1996).

Subraimani et al., "Expression of the Mouse Dihydofolate Reductase Complementary Deoxyribonucleic Acid in Simian Virus 40 Vector", *Mol. Cell. Biol.*, vol. 1, pp.854–864, (1981).

Lusky et al., "Inhibition of SV40 replication in simian cells by specific pBR322 DNA sequences", *Nature* vol. 293, pp. 79–81, (1981).

Fiddes et al., "The Gene Encoding the Common Alpha Subunit of the Four Human Glycoprotein Hormones" *Journal of Molecular and Applied Genetics*, vol. 1, pp.3–18, (1981).

Hamer et al., "Regulation In Vivo of a Cloned Mamalian Gene Cadmium Induced the Transcription of a Mouse Metallothionein Gene in SV40 Vectors", *Journal of Molecular and Applied Genetics*, vol. 1, pp.273–288, (1982).

Qin et al., "Infectious" Transplantation Tolerance, *Science*, vol. 259, pp.974–977, (1993).

Delaney et al., "Allogeneic Hematolymphoid Microchimerism and Prevention of Autoimmune Disease in the Rat" *J. Clin. Inves.*, vol. 97, pp.217–225, (1996).

Kernan et al., "Graft Rejection in Recipients of T–Cell–Depleted HLA–Nonidentical Marrow Transplants for Leukemia", *Transplantation*, vol. 43, No. 6, (1987), pp. 842–847.

Kozarsky et al., "Gene therapy: adenovirus vectors", *Current Opinions Genet. Dev.*, vol. 3, pp.499–503, (1993).

Barr et al., "Efficient catheter–mediated gene transfer into the heart using replication–defective adenovirus", *Gene Therapy*, vol. 1, 51–58, (1994).

Stratford–Perricaudet et al., "Widespread Long–term Gene Transfer to Mouse Skeletal Muscles and Heart" vol. 90, pp.626–630, (1992).

Rosenfeld et al., "In Vivo Transfer of the Human Cystic Fibrosis Transembrane Conductance Regulator Gene to to the Airway Epithelium", *Cell*, vo.68, pp.143–155, (1992).

Lemarchand et al., "Adenovirus–mediated transfer of a recombinant human –antitrypsin cDNA to human endothelial cells", *Proc. Natl. Acad. Sci*, vol. 89, pp. 6482–6486, (1992).

Tripathy et al., "Stable delivery of physiologic levels of recombinant erythroprotein to the systemic circulation by intramuscular injection of replication–defective adenovirus", *Proc. Natl. Acad. Sci.*, vol. 91 pp.11557–11561, (1994).

Bi et al., "In Vitro Evidence That Metabolic Cooperation Is Responsible for the Bystander Effect Observed with HSV tk Retroviral Gene Therapy", *Human Gene Therapy*, vol. 4, pp.725–731, (1993).

Berke, "The function and Mechanisms of action of cytolytic lymphocytes", Chapter 28, pp.972–974, Fundamental Immunology edited by W.E. Paul, (1993).

Huard et al., "Cellular expression and tissue distribution of the human LAG–3–encoded protein, an MHC class II ligand", *Immunogenetics*, vol. 39, pp.213–217, (1994).

* cited by examiner

METHODS FOR PREVENTING GRAFT REJECTION IN TRANSPLANTATION AND FOR PRODUCING A UNIVERSAL GENE THERAPY HOST CELL USING LYMPHOCYTE ACTIVATION (LAG-3)

CROSS REFERENCE TO RELATED APPLICATION

The present application is the national stage under 35 U.S.C. 371 of PCT/EP96/05280, filed Nov. 29, 1996.

FIELD OF THE INVENTION

The present invention relates to methods for preventing graft rejection of transplantated organs, tissues or cells, in particular to such methods which comprise engineering a cell type to express a LAG-3 protein when transplanted in a host. More particularly, the invention relates to the production of a universal gene therapy host cell expressing the LAG-3 protein on its surface.

DESCRIPTION OF THE BACKGROUND ART

The lymphocyte activation gene (LAG-3) is a member of the immunoglobulin superfamily, that is selectively transcribed in human activated T (both $CD4^+$ and $CD8^+$) and NK cells (Triebel et al, 1990 ). The sequence data, the compared exon/intron organization, and the chromosomal localization revealed that LAG-3 is closely related to CD4 (Baixeras et al, 1992). The close relationship between LAG-3 and CD4 was further strengthened by the demonstration that both share the same ligand, i.e., MHC class II molecules (Baixeras et al, 1992). However, in contrast to CD4, LAG-3 does not bind the human immunodeficiency virus gp120 (Baixeras et al, 1992). In vivo, LAG-3 expression was neither found in primary lymphoid organs, such as spleen, mucosa-associated lymphoid tissue or normal lymph nodes. However, it was readily detected in inflamed tonsils, or lymph nodes with follicular hyperplasia, supporting the view that even in vivo LAG-3 is expressed following activation (Huard et al, 1994A). Antigen-specific stimulation of T-cell clones in the presence of anti-LAG-3 monoclonal antibody (mAb) led to increased thymidine incorporation, higher expression of activation marker CD25 and enhanced cytokine production (Huard et al, 1994B).

Accordingly, addition of a soluble recombinant form of LAG-3 inhibited antigen-specific T-cell proliferation, suggesting a regulatory role of LAG-3 in $CD4^+$ T-lymphocyte activation (Huard, 1996) and its involvement in extinguishing ongoing immune responses. Recently, it has been shown that LAG-3 also acts as a co-receptor for NK cells and defines different modes of tumor cell killing controlled by the innate immune system (Miyazaki et al., 1996).

The mechanics by which a T cell response to a foreign (allogeneic or xenogeneic) protein or cell or organ is mounted are fairly well understood. Antigen presenting cells (APCs) are attracted to areas of inflammation or damage (that may be induced by surgical transplantation). The repertoire of T cells in the periphery is constantly surveying tissues for evidence of pathogens or the presence of foreign (allo- or xenogeneic) tissue. Once any of these warning signals are recognized, the APCs engulf the protein, digest it and present it to the host's immune system.

Allogeneic or syngenic tumor cells have been engineered to express viral IL-10 which induces local anergy to the tumors. Such a treatment did not affect the rejection of a non-transduced tumor at a distant site ( Suzuki et al., 1995). IL-10 delivered locally is thought to shift the T cell repertoire reactive to the transplanted cells to a Th2 phenotype that is not cytolytic and may even be protective.

Cells naturally expressing the Fas ligand have been transplanted across allogeneic or exogeneic barriers without immunosuppression. Surveillance of the site of implantation by host T cells results in their killing when contacted by Fas ligand (Bellgrau et al., 1995). Moreover, rejection of pancreatic islet allografts has been prevented by the cotransplantation of syngeneic myoblasts genetically engineered to express the Fas ligand (Lau et al., 1996)

The immune system is well equipped to rapidly identify foreign, diseased or inflamed tissue and rapidly destroys it. This has always been a major barrier to tissue, organ and cell transplantation as well as gene therapy. Major problems are generally associated with chronic immunosuppression, encapsulation or immunoisolation. The unwanted side effects of chronic immunosuppression include increased susceptibility to opportunistic infection and tumor formation.

The desire for long-term acceptance of grafted tissue in the absence of continuous immunosuppression is a long-standing goal in human medicine.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It has now been found that transplantation of cells that express a LAG-3 protein on their surface results in the protection from graft rejection by the host's immune system.

The present invention thus provides a genetically engineered cell which may be part of a tissue or organ to be transplanted, comprising DNA encoding a transmembrane LAG-3 protein on its surface, resulting in the protection from graft rejection by the host's immune system, the DNA being genomic DNA or cDNA. Said DNA can be exogenous or, in a particular embodiment of the invention, the endogenous DNA, whose expression is activated or modified through the targeted insertion of a regulatory sequence and/or an amplifiable gene by homologous recombination. The LAG-3 protein is a protein which is recognized by antibodies directed against LAG-3.

When the cell is part of the tissue or organ to be transplanted, transfection of the LAG-3 DNA can be accomplished directly on the tissue or organ to be transplanted.

In particular, the cell is a universal gene therapy host cell, suitable, for example, for any kind of somatic or "ex vivo" gene therapy.

In a specific embodiment, the gene therapy host cell further comprises exogenous DNA encoding a therapeutic agent of interest, and the genetically engineered cells are employed as a therapeutic agent. The term "therapeutic" as used herein, includes treatment and/or prophylaxis.

In a further embodiment, the gene encoding a therapeutic agent of interest is present in the genome of the cell and the cell further comprises exogenous DNA encoding a regulatory sequence or an amplifiable gene for activating or modifying the expression of the endogenous gene of interest.

The genetically engineered cell of the invention can, anyway, contain the exogenous LAG-3 DNA only, to be used in a mixture with other gene therapy host cells containing the therapeutic DNA of interest.

The cell of the present invention is preferably selected from myoblasts, fibroblasts, hematopoietic stem cells, embryonic stem cells, foetal liver cells, umbilical vein endothelial cells and CHO cells.

Cells as above, deriving from transgenic animals, are also within the scope of the present invention.

It is a further object of the present invention the use of a transmembrane LAG-3 protein, including muteins and variants thereof, expressed on the surface of the cells, in the manufacture of a medicament to induce protection from graft rejection by a host's immune system.

Furthermore, the present invention provides the use of a cell comprising DNA encoding a transmembrane LAG-3 protein, expressed on the surface of the cell, in the manufacture of a medicament to induce protection from graft rejection by a host's immune system.

The use of said cell expressing LAG-3 on its surface, in the manufacture of a medicament to be mixed with cells, tissues or organs to be transplanted, to induce protection from graft rejection by a host's immune system, is also within the scope of the present invention.

DETAILED DESCRIPTION OF THE INVENTION

Figure 1:
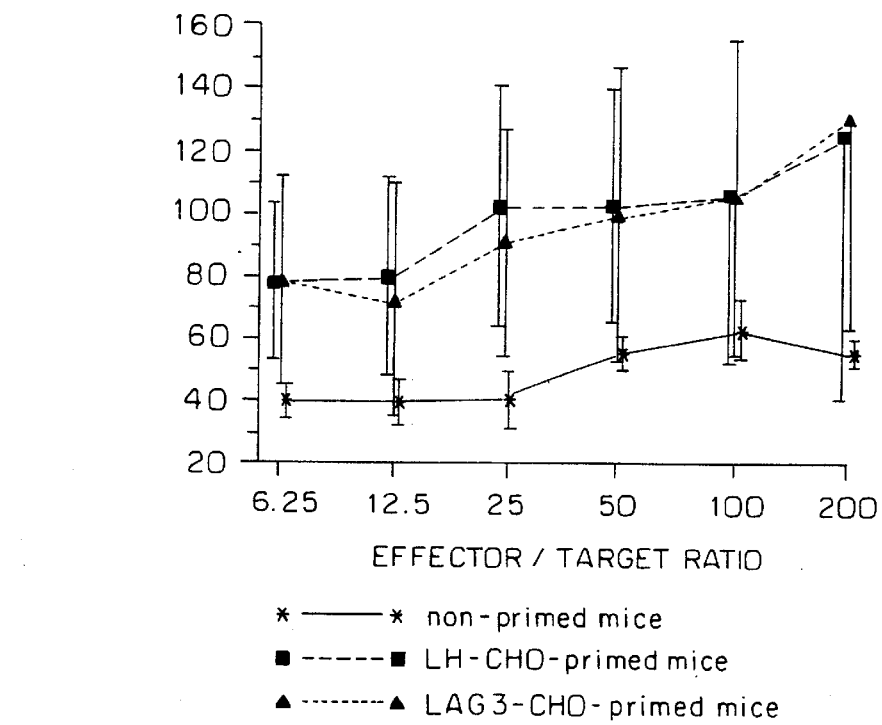
FIG. 1—Cytotoxic activity versus LH-CHO cells of splenocytes from mice primed with LAG-3-CHO or LH-CHO cells. The mean value (±SD) from 5 mice primed as indicated in the legend; 2 non-primed mice were also evaluated.

Hundreds of thousands of people die each year as a result of a heart, kidney, liver, lung or pancreas failure. The single most effective therapy is transplantation.

Therapy associated to transplantation of cells, tissues or organs induces a general immuno-protective state in the host relative to the engrafted cell, tissue or organ. It is desirable to establish graft specific protection against rejection by the host's immune system particularly in allogeneic transplantation, xenogeneic transplantation and gene therapy. Also, it is desirable to inhibit tolerance to tumor tissue or otherwise allow the host's immune system to attack tumor tissue.

Accordingly, the present invention is directed to all of the methods described above for using the finding that transplantation of cells or tissues which express a transmembrane LAG-3 protein results in the protection of graft rejection by the host's immune system.

The invention employs the newly discovered gene and protein, LAG-3, that is normally expressed on activated T cells and activated NK cells.

The definition "transmembrane LAG-3 protein" as used herein refers to any transmembrane protein containing the extracytoplasmatic domain of LAG-3, its salts, functional derivatives, precursors and active fractions as well as its active mutants and its active variants, which are all expressed on the surface of a cell.

The definition also refers to a transmembrane protein expressed in its natural state or can be fused, for example by genetic engineering, to another protein, such as a glycosyl phosphatidylinositol anchor or any relevant fragments of another transmembrane protein, for example TNF-receptor, MPL-ligand or a transmembrane immunoglobulin.

The definition "salts" as used herein refers both to salts of the carboxyl-groups and to salts of the amino functions of the compound obtainable through known methods. The salts of the carboxyl-groups comprise inorganic salts as, for example, sodium, potassium, calcium salts and salts with organic bases as those formed with an amine as triethanolamine, arginine or lysine. The salts of the amino groups comprise, for example, salts with inorganic acids as hydrochloric acid and with organic acids as acetic acid.

The definition "functional derivatives" as herein used refers to derivatives which can be prepared from the functional groups present on the lateral chains of the amino acid moieties or on the terminal N- or C- groups according to known methods and are comprised in the invention when they are pharmaceutically acceptable, i.e. when they do not destroy the protein activity or do not impart toxicity to the pharmaceutical compositions containing them. Such derivatives include, for example, esters or aliphatic amides of the carboxyl-groups and N-acyl derivatives of free amino groups or O-acyl derivatives of free hydroxyl-groups and are formed with acyl-groups as, for example, alcanoyl- or aroyl-groups.

The "precursors" are compounds which are converted into LAG-3 in the human or animal body.

As "active fractions" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of LAG-3 as medicament.

Preferred "active fractions" are soluble fractions from the extracellular portion of the LAG-3 protein, including one or more of the four domains, D1, D2, D3, D4, of the extracytoplasmatic domain of LAG-3.

The definition "active mutants" as used herein refers to other proteins or polypeptides wherein one or more amino acids of the structure are eliminated or substituted by other amino acids, or one or more amino acids are added to that sequence in order to obtain polypeptides or proteins having the same activity of LAG-3. For example, Arg 73 and/or Arg 75 and/or Arg 76 can be substituted with a different amino acid, preferably with Glu.

The "active variants" of LAG-3 are differentially spliced variants as well as all primary gene transcripts, which derive from alternative splicing mechanisms at different cleavage sites of the gene. Preferred variants are soluble or transmembrane proteins lacking the D3 and/or D4 domains of the extracellular portion of LAG-3, optionally containing a few additional amino acids after the D2 or the D3 domain.

The expression of the transmembrane LAG-3 protein on the surface of a cell is verified by immunoreactive methods. The transmembrane protein is recognized, for example, by the anti-LAG-3 antibodies 11E3 (Deposit No. CNCM I-1612), 17B4 (Deposit No. CNCM I-1240) or 15A9 (Deposit No. CNCM I-1239).

The present invention also refers to a mixture of polypeptides and derivatives as said above.

When used in the present specification and claims, the expressions "LAG-3", "LAG-3 protein" or "LAG-3 molecule" are intended to include natural, synthetic and recombinant forms of the polypeptide as well as all the definitions reported above.

The cells of the present invention can be selected from primary or secondary cells. As used herein, the term primary cell includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

The present invention includes primary and secondary somatic cells, such as fibroblasts, keratinocytes, epithelial cells, endothelial cells, glial cells, neural cells, formed elements of the blood, muscle cells, other somatic cells which can be cultured and somatic cell precursors, which have been transfected with exogenous DNA which is stably integrated into their genomes or is expressed in the cells episomally. The resulting cells are referred to, respectively, as transfected primary cells and transfected secondary cells.

When the gene encoding a LAG-3 molecule is inserted into mammalian cells and the cells are transplanted into an allogeneic or xenogeneic host, they are recognized by the host immune system but an immune response is not mounted.

The host immune system becomes unable to reject the cells that would otherwise have been rejected had they not been engineered to express the LAG-3 molecule on their cell surface. LAG-3 can also be expressed upon the cell surface of an unrelated cell type and mixed with the cells or tissues to be transplanted with similar results to those described above. Thus, this invention relates to the transplantation of cells, tissues, or organs without general immunosuppression.

These cells, tissues or organs are transplanted to provide proteins or perform certain functions to treat certain diseases. They are accepted by the host by the use of a technique in which LAG-3 is presented to the host's immune system.

Prevention of graft rejection of specific cells, tissues or organs can also be achieved in recipients by co-administration of fibroblasts or other primary or secondary cells that have been engineered to express LAG-3. This protective state may be due to local or general inhibition of mechanisms mediating immune responses. This protective state may be due to anergy, deletion, non-responsiveness, tolerance or prevention of cell-mediated cytotoxicity. Once a protective state is established, it endures for extended periods of time, even permanently due to a phenomenon such as infectious tolerance (Qin et al., 1993).

The invention can be utilized for transplantation of cells tissues, organs or host cells to deliver genes or gene products for a variety of human medical needs.

LAG-3 gene expression can be induced by standard recombinant DNA techniques or by techniques that employ homologous recombination to activate the endogenous LAG-3 gene. The cell types can be obtained from transgenic animals that have the LAG-3 gene expressed in specific tissues or in unrelated cells by any method. Such cells could then be mixed with the cells in which protection from graft rejection is desired. This suggests that local secretion of the immuno-protective molecule LAG-3 does not act systemically. LAG-3 transduced, non-transformed fibroblasts yield similar responses in vivo. The immuno-protective effects of the innoculum of LAG-3 transduced fibroblasts are dose dependent but independent of the source of the LAG-3 molecule.

The co-administration of LAG-3 expressing cells inactivates donor T cells while at the same time preventing attack from the host immune system. This treatment induces specific anergy, tolerance or otherwise protection from cell-mediated cytotoxicity in the recipient which can then result in a long-term change in the immune microenvironment allowing protection against autoreactive T cells. This can be done by co administration of a small number of allogeneic bone marrow cells from a healthy donor along with human allogeneic cells that have been engineered to express LAG-3. This results in a decrease in autoreactive T cells through the development of microchimerism ( Delaney et al., 1996).

Humans with specific diseases or deficiencies can benefit from the allogeneic transplantation of many different cells, tissues or organs. For example organs, such as liver, kidney, heart, pancreas, small bowel are commonly transplanted and cells such as islets, neural tissue for the treatment of Parkinson's disease or focal epilepsy, hematopoietic stem cells as a treatment for chemotherapy or radiation therapy, normal hepatocytes to treat hypercholesterolemia, cardiac cells for myocardial infarction, muscle cells for muscular dystrophy are suitable for transplantation.

Allogeneic bone marrow transplants have been difficult to accomplish for a variety of reasons. They include: graft rejection, infection due to opportunistic infections as a result of contamination of the graft or immunosuppressive drugs, or other reasons. Rejection may be due to the resistance of the recipient to bone marrow engraftment by donors and the tendency of competent immune cells to attack the recipient i.e. (Graft-versus-host disease). GVHD may be controlled by the depletion of the graft of T cells or the co-administration of immunosuppressant drugs. Engraftment is reduced when T cells are eliminated.

As a result of the T cell elimination, there is a higher incidence of graft failure. It is thought that they may provide an important function for engraftment such as the elaboration of cytokines (Keman et al., 1987).

It has been shown that only small numbers of allogeneic but healthy bone marrow cells can reduce or even prevent the occurrence of autoimmune disease in experimental models. However, treatments such as these result in graft-versus-host disease.

Bone marrow transplantation has also been used as a method to eradicate certain tumors. This is purportedly due to the ability of allogeneic T cells to recognize and kill tumor tissue, e.g. in graft-versus-leukemia.

In all the above cases general immunosuppression is avoided if the cells or organs to be transplanted are engineered with a gene encoding LAG-3, so as to express a LAG-3 protein when transplanted in a host and induce graft protection.

A first problem in allogeneic transplantation is the lack of transplantable human tissue and nowadays demand for organs far exceeds supply. Although still regarded as an experimental procedure, xenotransplantation is considered to be a viable alternative to allotransplantation. Animals such as pigs or baboons are now being considered as organ or cell donors. Protection from graft rejection may be essential for successful clinical use of organs from different species. Host resistance can be overcome, at least partially, for example, using antibodies against human CD4, CD8, NK cells, or microencapsulating the animal cells to be transplanted. According to the present invention, the animals can be transgenically altered to express LAG-3 gene in certain cell types like the islet cells by the use of the insulin gene promoter and targeting system or other tissue specific maker system.

The expression of LAG-3 on tumor tissue is thought to play an important role in the resistance to cell-mediated attack against tumor tissue from the host's immune system.

According to a particular embodiment of the present invention, through the use of gene therapy or ex vivo treatment of a small amount of tumor tissue and reimplantation, the tumor tissue can be engineered to express antisense LAG-3 molecules or ribozymes specific for LAG-3 message. This would allow the immune system to react to the tissue and learn to destroy it. A small amount of the tumor tissue can also be treated with an antibody to LAG-3 to prevent T cell inhibition induced by LAG-3 and allow induction of cellular and humoral immunity against it.

Gene therapy is now highly desirable for the treatment of a variety of diseases, including but not limited to adenosine deaminase deficiency (ADA), sickle cell anemia, thalassemia, hemophilia, diabetes, alpha-antitripsin deficiency, brain disorders such as Alzheimer's disease and other illnesses such as growth disorders and heart diseases, for example those caused by alterations in the way cholesterol is metabolized, and defects of the immune system.

Different cells can be used for transplantation in individuals in need, for example myoblasts for dystrophin delivery, cells that secrete material such as TPO, GH, EPO, Factor IX or other factors, blood cells for the treatment of inheritable blood disorders and other primary human or animal cells, such as endothelial cells, epitelial cells, connective tissue cells, fibroblasts, mesenchymal cells, mesothelial cells and parenchymal cells.

Results of gene therapy have not been very satisfying due to a number of problems. Even the most advanced trials in which a young girl has been treated with the gene for adenosine deaminase (ADA), the patient still receives weekly injection of PEG-ADA for fear that the gene therapy alone is ineffective.

One of the shortcomings of gene therapy protocols today is the requirement of individual production of host cells to attempt to prevent rejection of the cell by the host immune system. Gene therapy must be performed on an individual by individual basis. Further, the expression of transgenes is usually found to be transient due to the expression of other viral proteins which engage the host immune system even through the use of autologous cells for gene therapy.

Crippled adenoviral vectors are used but these have problems due to the other viral proteins that are expressed that evoke an immune response. Large concentrations of virus, even a crippled one, stimulate an inflammatory response and an immune attack. The host cell immune system will remember the viral vector so that future administrations will be even less effective.

Viral protein E1 deleted replication defective adenoviruses are routinely employed in gene therapy protocols. Unfortunately, they have only transiently effective in adult, immunocompetent hosts presumably as a result of an immune response directed against adenoviral or recombinant proteins (Kozarsky and Wilson, 1993; Barr et al., 1992; Stratford et al., 1992; Rosenfeld et al., 1992; Lemarchand et al., 1992). Therefore, there is a great need to develop new vectors that are not so immunogenic or methods that allow for immunological protection of the genetically engineered cells.

These vectors are prepared at high titer up to $10^{11}$ plaque forming units per ml and infect many replicating and non-replicating cells. Use replication defective adenoviruses to deliver physiological levels of recombinant protein to systemic circulation. The LAG-3 gene is preferably under the transcriptional control of the ubiquitously active cellular EF1α promoter and the 4F2HC enhancer (Tripathy et al., 1994).

Attempts have been made to avoid this problem by encapsulating the cells and by immunosuppressing the host.

With the methods herein described, xenogeneic or allogeneic cells can be used as gene therapy hosts expressing a LAG-3 molecule on their surface, so as to induce protection from graft rejection by the host's immune system. They are, for example, myoblasts, fibroblasts, hematopoietic stem cells, embryonic stem cells, foetal liver cells, umbilical vein endothelial cells, or CHO cells. The gene therapy host cells can also be engineered to express the herpes simplex thymidine kinase gene. Such cells can be specifically destroyed by addition of gancylovir.

The tk-gancyclovir sensitive cells have a significant advantage over non-sensitive cells, in that they can be deleted at any time (Bi et al., 1993).

The universal host cell that is prepared according to the present invention to express LAG-3 and the Hsv-tk gene on its cell surface thus allows for the generation of a universal gene therapy host cell that can be implanted without immunosuppression and can be destroyed at any point should its activity no longer be required.

The allogeneic or xenogeneic gene therapy host cells of the present invention can be engineered to express a transgene and/or the LAG-3 gene through the use any method of gene transfer such as but not limited to replication defective viruses, adeno-associated virus, high efficiency retrovirus, direct injection of DNA into bone marrow, electroporation, calcium phosphate transfection, microinjection, encapsulation into liposomes or erythrocyte ghosts. Cells that express LAG-3, such as myoblasts or CHO cells may be co-administered with cells expressing a protein of interest to be permanently engrafted. If transient LAG-3 exposure is adequate, then the LAG-3 transfected myoblasts or CHO cells can contain a suicide gene, such as tk, as reported above, so that they can be removed by treatment with gancyclovir.

This method can be used to restore normal function by administration of a gene or gene product or the removal or inactivation of a gene that is dangerous to the body (such as an oncogene). This goal can also be achieved by implanting cells that deliver ribozymes or antisense cDNA to inhibit the production of unwanted protein such as HIV proteins or growth factors. The method can be used to correct enzyme deficiencies such as Gaucher's disease or ADA deficiency.

According to a further embodiment the present invention is directed to a method for gene therapy comprising: (i) inserting into the human or animal cells of choice the gene needed for therapy and the gene encoding a LAG-3 molecule; and (ii) introducing cells resulting from step (i) into the patient. Alternatively, the genes as above may be inserted into a tissue organ of a patient, in vivo, by direct transfection of the genes as such, or in a vehicle which targets such tissue or organ.

For example, the claimed expression system allows for the injection of a naked DNA or of a viral vector directly into a cell group like muscle cells or administered directly into the airways (for instance to treat cystic fibrosis). The construct contains not only the gene of interest (such as the conductance regulator (CFTR cDNA) but also the LAG-3 gene to be co-expressed on the cell type to prevent the possible humoral immune responses to, for example, the adenovirus capsid proteins which would limit the efficacy of repeat administrations. Gene transfer into hematopoietic stem cells can be used for the administration of multi-drug resistance genes to combat one of the side effects of chemotherapy-suppression of rapidly dividing immune cells. Retroviral vectors can be used in combination with cytokines such as Steel factor, kit ligand, IL3, GM-CSF, IL6, G-CSF, LIF, IL12 to encourage stem cells to divide.

The cells of choice can be cotransfected with genes encoding other immune suppressive agents, such as IL10, TGFβ, Fas ligand, in addition to the LAG-3 gene.

As a particular embodiment of the present invention, the methods described above are used to treat the recipient with a small number of cells of interest engineered to express the LAG-3 gene which will make the host tolerant to a next administration of cells, tissues or organs due to infectious tolerance by the host's immune system.

The invention will now be described by way of illustration only with reference to the following examples:

EXAMPLE 1

Methods
Generation of CHO Cells Expressing Transmembrane LAG-3

LAG-3 cDNA was excised as a 1620 bp Xho fragment from pCDM8 plasmid (Invitrogen San Diego Calif.) and purified by agarose gel electrophoresis.

Figure 3:
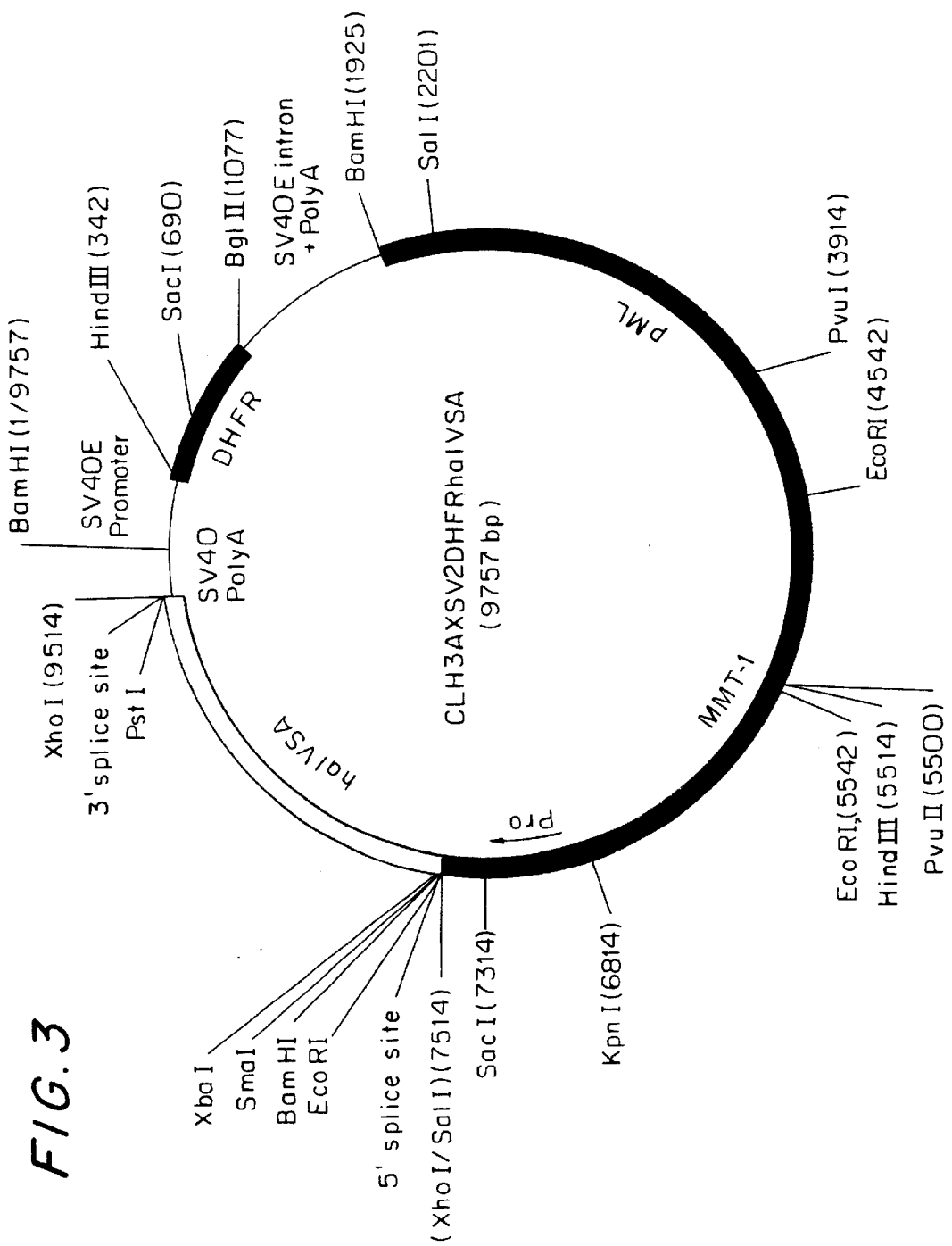
FIG. 3—Map of the Dα mammalian expression vector. Abbreviation used: DHFR, dehydrofolate transcription unit (Subraimani et al., 1981); pML, derivative of pBR322 (Lusky and Botchan, 1981); hAIVSA, fragment from intron A of the α subunit of human glycoprotein hormones (Fiddes and Goodman, 1981); MMT-1, promoter of the mouse metallothionein 1 (Hamer and Walling, 1982).

The fragment was subcloned into the pCLH3AXSV2DHFRhαIVSA (Dα) mammalian expression vector (FIG. 3) digested with Xho. CHO-DUKX (DHFR⁻) cells were transfected with the DαLAG-3 construct by CaPO$_4$ precipitation method. Transfected cells were grown in selection medium (MEM medium without deoxy- and ribonucleotides +10% dialyzed fetal bovine serum +1% L-glutamine +0.02 $\mu$M metothrexate). The expression of LAG-3 was checked by western blotting on lysed cell membrane preparations and periodically by flow cytometric analysis using anti-LAG-3 monoclonal antibody 17B4.
Transplantation of CHO Cells into Mice Chinese hamster ovary (CHO) cells, either untransfected (wild type) or transfected with full length human LAG-3 or human LH cDNA, were detached from plastic flasks and suspended in Dulbecco's modification of minimum essential medium (DMEM) at a concentration of $1.75 \times 10^7$ cells/ml. Twenty-six C57BL/6 female mice aged 7–9 weeks were distributed into 7 groups as indicated in Table 1 and 200 ml of the cell suspension indicated, containing $3.5 \times 10^6$ cells were injected subcutaneously in the right flank of each animal. In groups 3, 6 and 7 the same mouse received LAG-3-transfected cells in the right flank and controll cells (LH-transfected or untransfected) in the other. Four days after the injection the mice were sacrificed by $CO_2$ inhalation and the skin was opened to examine the site of injection.

TABLE 1

Experimental groups

| Group | No. of mice | Mouse Identification | CHO cells injected in the right flank | CHO cells injected in the left flank |
|---|---|---|---|---|
| 1 | 5 | 1 to 5 | wild type | — |
| 2 | 5 | 6 to 10 | LAG-3 | — |
| 3 | 5 | 11 to 15 | LAG-3 | wild type |
| 4 | 2 | 16 and 17 | LH | — |
| 5 | 5 | 18 to 22 | LAG-3 | — |
| 6 | 2 | 23 and 24 | LAG-3 | wild type |
| 7 | 2 | 25 and 26 | LAG-3 | LH |

Evaluation of Cytotoxicity Against CHO Cells

Five C57BL/6 female mice per group were injected s.c. with $4 \times 10^5$ CHO cells transfected either with human LH or human LAG-3 cDNA. After 14 days the mice were sacrificed and the spleen were removed to obtain splenocyte suspensions. Splenocyte suspensions (effectors) were diluted in culture medium (RPMI 1640+10% fetal bovine serum + antibiotics) at $10^7$ cells/ml and plated in triplicate at different dilutions to obtain the various effector to target ratios; 2 plates were prepared for each suspension. Target cells at $5 \times 10^3$ cells/100 $\mu$l (either LH- or LAG-3-trasnsfected cells), labelled with $^{51}Cr$, were added to the plates (one plate for each target). After 20 hours at 37° C., 20 $\mu$l of supernatant were taken from each well and the release of $^{51}Cr$ was evaluated by liquid scintillation. The cytotoxic activity was calculated as percentage of lysis according to the following formula:

$$\% = \frac{(CPMsample - CPMspont)}{(CPMmax - CPMspont)} \times 100$$

where spont and max indicate the wells with culture medium (spontaneous Cr release from the target cells) and Triton X 1% (maximum Cr release) replacing the effector suspension, respectively.

Results
Transplantation of CHO Cells into Mice

Most mice receiving LAG-3-transfected cells showed a white nodule at the site of injection which did not appear in the animals treated with wild type CHO or in those receiving LH-transfected CHO cells. The injection of wild type CHO cells caused the appearance of a diffuse hemorrhage in the injection site in the majority of the mice. This phenomenon was less evident in animals receiving LH-transfected cells. In the mice injected with both wild type and LAG-3 transfected CHO cells at different sites this nodule was apparent only in the site injected with the latter while an hemorrhage appeared in the other site (Table 2).

Histological analysis performed previously in a similar experiment showed the presence of heterologous cells in the nodules. The results of the experiment are shown in the attached pictures (see Table 1 for the identification of the mice) and summarized in Table 3.

TABLE 2

| Injected cells | No. of mice | Frequency (number of positive findings/ total number of flanks injected): | |
|---|---|---|---|
| | | hemorrhage | nodule |
| LAG-3 | 10 | 1/10 | 9/10 |
| wild type | 5 | 3/5 | 0/5 |
| LH | 2 | 1/2 | 1/2 |
| LAG-3 + wild type* | 7 | 0/7 (a) 5/7 (c) | 7/7 (a) 1/7 (c) |
| LAG-3 + LH* | 2 | 0/2 (b) 1/2 (a) | 0/2 (b) 2/2 (a) |

*Each cell type alone was injected in one side flank
(a) = LAG-3 side
(b) = LH side
(c) = WT side

TABLE 3

| Injected cells | Frequency (number of positive findings/ total number of flanks injected): | |
|---|---|---|
| | hemorrhage | nodule |
| CHO wild type | 8/12 (67%) | 0/12 (0%) |
| CHO LH | 1/4 (25%) | 1/4 (25%) |
| CHO LAG-3 | 2/19 (11%) | 16/19 (84%) |

Cytotoxicity Against CHO Cells

Figure 2:
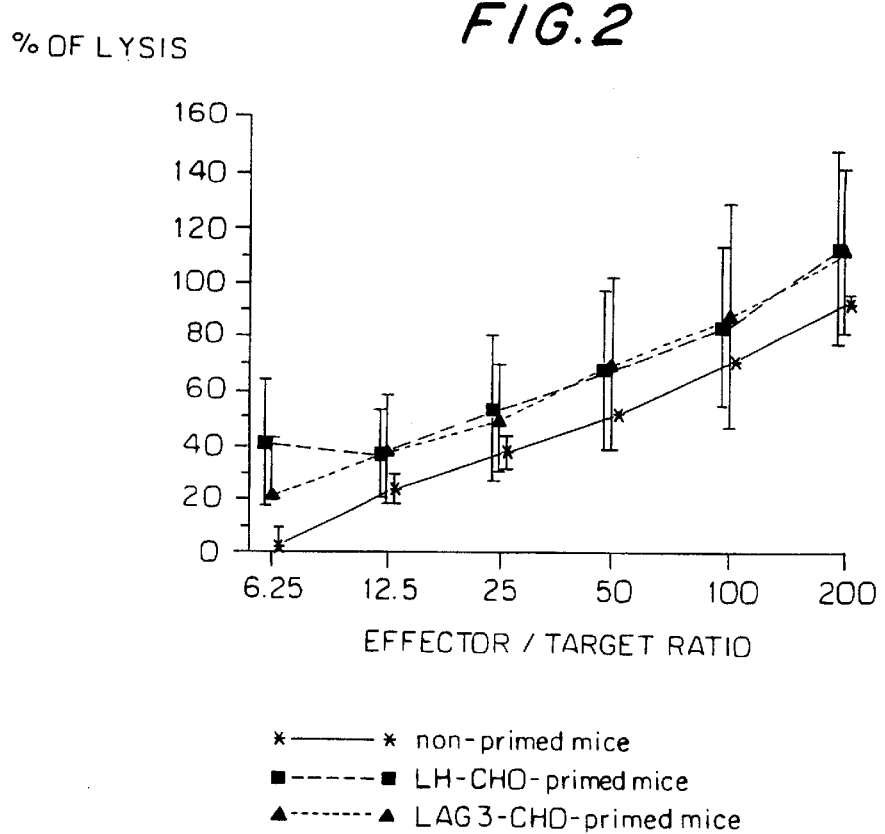
FIG. 2—Cytotoxic activity versus LAG-3-CHO cells of splenocytes from mice primed with LAG-3-CHO or LH-CHO cells. The mean value (±SD) from 5 mice primed as indicated in the legend; 2 non-primed mice were also evaluated.

The expression of LAG-3 on the surface of CHO cells did not affect the ability of the mice to be immunologically primed against the xenogeneic cells. In fact, the splenocytes from mice injected with LAG-3-CHO cells lysed both target cells as efficiently as those from mice primed with LH-CHO cells and better than non-primed mice. However the expression of LAG-3 on the cell surface was associated with a reduced sensitivity to the cytotoxic activity induced by immunization of the mice versus the target as can be seen by comparing the percentage of lysis in FIG. 1 and FIG. 2. The "natural" cytotoxicity, exerted by splenocytes from non-primed mice, is not reduced by surface expression of LAG-3. This indicates that LAG-3 surface expression reduces the efferent branch of cytotoxic T lymphocyte (CTL) activity. CTL are one of the effectors playing a main role in the rejection of transplantated organs (G. Berke, 1993) thus the inhibition of their function can prolong the survival of allografts.

REFERENCES

1. Triebel et al., J. Exp. Med., 171: 1393, 1990
2. Baixeras et al., J. Exp. Med., 176: 327, 1992
3. Huard et al., Immunogenetics, 39: 213, 1994A
4. Huard et al., Eur. J. Imunol., 24: 3216, 1994 B.
5. Huard et al., Eur. J. Immunol., 26: 1180–1186, 1996
6. Miyazaki, et al., Science, 272: 405–408, 1996
7. Susuki et al., J. Exp. Med., 182: 477–486, 1995
8. Bellgrau et al., Nature, 377: 630–632, 1995
9. Lau et al., Science, 273: 109–112, 1996
10. Subraimani et al., Mol. Cell. Biol., 1: 854–864, 1981
11. Luski and Botchan, Nature 293: 79–81, 1981
12. Fiddes and Goodman, J. Mol. Appl. Genetic 1: 3–18, 1981
13. Hamer and Walling, J. Mol. Appl. Genetic 1: 273–288, 1982
14. Qin et al., Science, 259: 974, 1993
15. Delaney et al., J. Clin. Inves., 97: 217–225, 1996
16. Kernan et al., Transplantation, 43: 842, 1987
17. Kozarsky and Wilson, Current Opinions Genet. Dev., 3: 499, 1993
18. Barr et al., Gene Therapy, 1: 51, 1992
19. Stratford et al., J. Clin. Inves., 90: 626, 1992
20. Rosenfeld et al., Cell 68: 143, 1992
21. Lemarchand et al., PNAS, 89: 6482, 1992
22. Tripathy et al., PNAS, 91: 11557, 1994
23. Bi et al., Human Gene Therapy 4: 725, 1993
24. Berke, The functions and mechanisms of action of cytolytic lymphocytes. Chapter 28 pages 972–974 in: Fundamental Immunology edited by W. E. Paul New York, 1993.

What is claimed is:

1. A process for inducing LAG-3 mediated protection from graft rejection of transplanted human cells, tissues or organs by a host immune system, comprising treating a human host patient at a graft site with a genetically engineered cell selected from the group consisting of human myoblasts and human fibroblasts, wherein said genetically engineered cell comprises DNA encoding a full length transmembrane LAG-3 protein, wherein the transmembrane LAG-3 protein is expressed on the surface of the genetically engineered cell and induces LAG-3 mediated protection from graft rejection of transplanted human cells, tissues, or organs by the immune system of the host.

2. A process as claimed in claim 1, wherein the genetically engineered cell is part of a tissue or organ to be transplanted.

3. A method for inducing LAG-3 mediated protection from graft rejection by a host immune system, comprising administering a genetically engineered cell, wherein said genetically engineered cell comprises DNA encoding a full length transmembrane LAG-3 protein and wherein the transmembrane LAG-3 protein is expressed on the surface of the genetically engineered cell, to a human host in need thereof at a graft site, wherein said genetically engineered cell is selected from the group consisting of human myoblasts and human fibroblasts and said administration induces LAG-3 mediated protection from graft rejection by the host immune system.

4. A method for inducing LAG-3 mediated protection from graft rejection by a host immune system, comprising:
   mixing a genetically engineered cell, wherein said genetically engineered cell comprises DNA encoding a full length transmembrane LAG-3 protein and wherein the transmembrane LAG-3 protein is expressed on the surface of the genetically engineered cell, with human cells, tissues or organs to be transplanted to form a mixture; and
   administering the mixture to a human host in need thereof at a graft site, wherein said genetically engineered cell is selected from the group consisting of human myoblasts and human fibroblasts and said administration induces LAG-3 mediated protection from graft rejection by the host immune system.

5. A method for inducing LAG-3 mediated protection from graft rejection by a host immune system, comprising:
   expressing a full length transmembrane LAG-3 protein on the surface of a human cell selected from the group consisting of human myoblasts and human fibroblasts; and
   administering said human cell to a human host in need thereof at a graft site, wherein said administration induces LAG-3 mediated protection from graft rejection by the host immune system.

* * * * *